US00PP19567P2

(12) United States Plant Patent
Heims

(10) Patent No.: US PP19,567 P2
(45) Date of Patent: Dec. 9, 2008

(54) ***BEGONIA* PLANT NAMED 'METALLIC MIST'**

(50) Latin Name: ***Begonia* hybrid**
Varietal Denomination: Metallic Mist

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/977,217

(22) Filed: Oct. 23, 2007

(51) Int. Cl.
*A01H 5/00* (2006.01)

(52) U.S. Cl. ..... Plt./343

(58) Field of Classification Search ..... Plt./343
See application file for complete search history.

*Primary Examiner*—Annette H Para
(74) *Attorney, Agent, or Firm*—Klarquist Sparkman, LLP

(57) ABSTRACT

A new and distinct form of *Begonia* plant characterized by maple shaped leaves which are heavily silvered, with red veins and backs, pink flowers, and excellent vigor.

1 Drawing Sheet

Botanical denomination: *Begonia* hybrid.
Variety designation: 'Metallic Mist'.
Parentage: *Begonia pedatifida*×*Begonia taliensis.*

BACKGROUND OF THE INVENTION

The present invention relates to a new and distinct cultivar of *Begonia,* of the family *Begoniaceae,* and given the cultivar name 'Metallic Mist'. This plant originated from planned cross between *Begonia pedatifida,* as the seed parent, and *Begonia taliensis,* as the pollen parent. All the seedlings in the cross had slightly different versions of maple-shaped leaves. The selection 'Metallic Mist' was made for its heavily silvered foliage with dark veins and red highlights, and vigor. The 'Metallic Mist' variety was identified in a greenhouse in Canby, Oreg. This combination of traits is unique in hardy *Begonia.*

SUMMARY OF THE INVENTION

This plant is characterized by:

1. Maple-shaped leaves which are heavily silvered, with red veins and backs;
2. Pink flowers; and
3. Excellent vigor.

The new variety has been reproduced only by asexual propagation (cuttings and tissue culture). Each of the progeny exhibits identical characteristics to the original plant. Asexual propagation by micropropagation as done in Canby, Oreg. shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers and leaf of *Begonia* 'Metallic Mist'.

FIG. 2 shows a one-and-a-half year old plant growing in a one gallon container in August in Canby, Oreg.

DETAILED PLANT DESCRIPTION

The following is a detailed description of the new *Begonia* cultivar based on observations of a one-year-old specimen grown in a greenhouse in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based or The Royal Horticultural Society Colour Chart.

Plant:

*Type.*—Herbaceous rhizomatous perennial.
*Form.*—Clumping, acaulescent.
*Cold hardiness.*—USDA Zone 7.
*Size.*—Grows to 15 cm tall to top of foliage and 35 cm wide.
*Vigor.*—excellent.
*Roots.*—Thickened (to 6 mm wide), branching, roots easily from divisions.

Leaf:

*Type.*—simple.
*Arrangement.*—Basal.
*Shape.*—Oblique and asymmetric.
*Lobing/Division.*—Palmately lobed, 5 to 7 main lobes, cut in ⅓.
*Venation.*—Palmate.
*Margins.*—Doubly serrate, mature leaves sometimes cupping.
*Apex.*—Acuminate.
*Base.*—Cordate, overlapping.
*Blade size.*—Grows to 18.5 cm wide and 20 cm long.
*Surface texture.*—Pubescent on top surface and on veins on bottom surface.
*Petiole description.*—Grows to 12.5 cm long and 4 mm wide, pubescent, Yellow Green 148A.
*Leaf color.*—Top side: New leaves Greyed Green 198B tinted Greyed Purple 187C with veins Green 139A but deeper green. Mature leaves between Greyed Green 189B and Greyed Green 188A with veins Greyed Green 189A but darker. Bottom side: Yellow Green 148B heavily tinted Greyed Purple 187B and vein Greyed Purple 187A.

Inflorescence:

*Type.*—Panicle.

*Number of flowers per panicle.*—6 to 10.

*Peduncle description.*—grows 15 cm long and 4 mm wide, glabrous, fleshy, between Yellow Green 152B and Grey Brown 199C; with 0 to 3 petiolate leaf-bracts which grow to 6 cm wide and 6.6 cm long and are other wise the same as the crown leaves.

*Pedicel description.*—25 to 32 mm long, 1.3 mm wide, fleshy, glabrous, Red 49D.

*Bloom period.*—June to July in Canby, Oreg.

Flower bud:

*Size.*—Staminate flowers 13 mm long and 10 mm wide prior to opening; pistillate flowers are 20 mm long and 15 mm wide.

*Color.*—White 155D with tips and edges, Red Purple 71B.

Flower:

*Type.*—Monoecious, bilaterally symmetrical.

*Pistillate flower.*—27 mm long and 29 mm wide overall; 3 to 4 fleshy tepals, irregularly grow to 17 mm long and 10 mm wide, ovate to broadly elliptical, tip and base obtuse, margins entire to undulate, glabrous on both sides, White 155B on the bottom half and darkening to Red Purple 67A at tip; ovary 29 mm wide and 15 mm deep, three winged, two equal and one longer, White 155B netted with Red Purple 67C, style 3 branched, 5 mm long and 7 mm wide overall, Yellow 9A, stigma 2 branched and twisted, 4 mm wide 4 mm long.

*Staminate flower.*—12 mm long and 5 mm wide, 4 tepals, 2 large outer tepals 12 mm long and 7 mm wide and inner tepals are 6 mm long and 5 mm wide; both are broadly ovate, entire, obtuse at tip and base, White 155B on bottom half darkening to Red Purple 67A at tip; stamen many, Yellow 11B, filament 1.2 mm long, anthers less than 1 mm, pollen none.

*Fragrance.*—None.

*Lastingness.*—A panicle blooms for about 2 weeks on the plant.

Fruit and seed: none, sterile.

Diseases and pests: *Begonia* species are susceptible to root rots. This new variety has no known immunities.

Comparison to parent plants:

Compared to *Begonia pedatifida,* the seed parent, *Begonia* 'Metallic Mist' has leaves that are less deeply lobed, darker green, and heavily silvered rather than green with red veins.

Compared to *Begonia taliensis,* the pollen parent, *Begonia* 'Metallic Mist', has thicker leaves that are more lobed and have a pink tinge to the new leaves and red backs.

I claim:

1. A new and distinct form of *Begonia* plant as hereby illustrated and described.

* * * * *

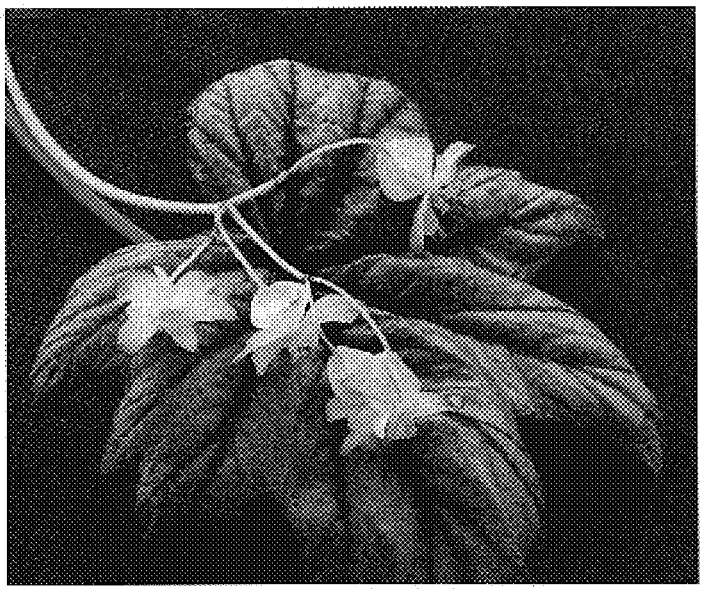
Figure 1 above, figure 2 below.
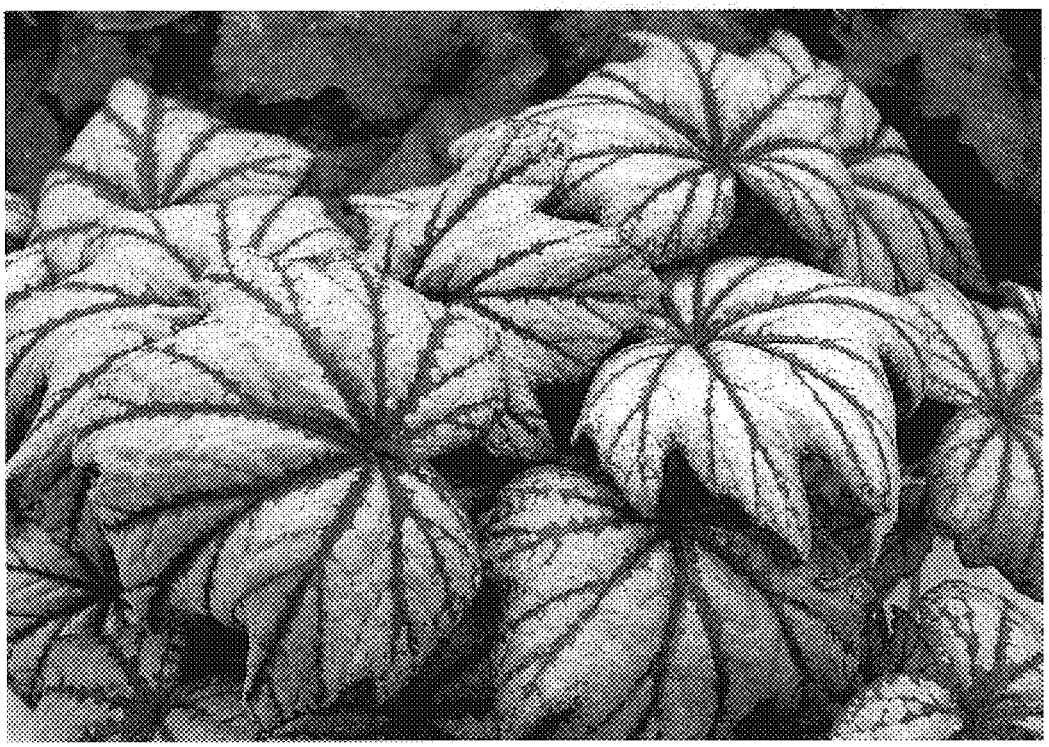

UNITED STATES PATENT AND TRADEMARK OFFICE

CERTIFICATE OF CORRECTION

PATENT NO. : PP 19,567 P2
APPLICATION NO. : 11/977217
DATED : December 9, 2008
INVENTOR(S) : Daniel M. Heims It is certified that error appears in the above-identified patent and that said Letters Patent is hereby corrected as shown below:

In the Specification:

Column 2, line 9, “based or” should be --based on--.

Signed and Sealed this

Twenty-fourth Day of February, 2009

John Doll

JOHN DOLL
*Acting Director of the United States Patent and Trademark Office*